United States Patent
Li et al.

(10) Patent No.: US 6,433,000 B1
(45) Date of Patent: Aug. 13, 2002

(54) COMPOUNDS FOR THE TREATMENT OF ESTROGEN-DEPENDENT ILLNESSES AND METHODS OF MAKING AND USING THE SAME

(75) Inventors: Pui-Kai Li, Galloway, OH (US); Kyle W. Selcer, Murrysville, PA (US)

(73) Assignee: Duquesne University of the Holy Ghost, Pittsburgh, PA (US)

(*) Notice: Subject to any disclaimer, the term of this patent is extended or adjusted under 35 U.S.C. 154(b) by 0 days.

(21) Appl. No.: 09/845,850

(22) Filed: Apr. 30, 2001

Related U.S. Application Data

(60) Division of application No. 09/536,331, filed on Mar. 24, 2000, now Pat. No. 6,288,107, which is a continuation-in-part of application No. 09/164,889, filed on Oct. 1, 1998, now Pat. No. 6,248,780.

(51) Int. Cl.[7] .................. C07D 209/44; C07C 309/34; A61K 31/21
(52) U.S. Cl. .................. 514/416; 558/48; 548/482; 514/506
(58) Field of Search .................. 548/482; 558/48

(56) References Cited

U.S. PATENT DOCUMENTS

| | | |
|---|---|---|
| 5,556,847 A | 9/1996 | Johnson et al. |
| 5,567,831 A | 10/1996 | Li |
| 5,571,933 A | 11/1996 | Li et al. |
| 5,604,215 A | 2/1997 | Reed et al. |
| 5,616,574 A | 4/1997 | Reed et al. |
| 5,763,432 A | 6/1998 | Tanabe et al. |
| 5,763,492 A | 6/1998 | Johnson et al. |
| 5,880,115 A | 3/1999 | Li et al. |
| 6,248,780 B1 * | 6/2001 | Li et al. .................. 514/510 |
| 6,288,107 B1 * | 9/2001 | Li et al. .................. 514/443 |

* cited by examiner

*Primary Examiner*—Johann Richter
*Assistant Examiner*—Ebenezer Sackey
(74) *Attorney, Agent, or Firm*—Debra Z. Anderson; Eckert Seamans Cherin & Mellott, LLC

(57) ABSTRACT

Novel sulfatase inhibitor/estrogen receptor blocker compounds useful in the treatment of estrogen dependent illnesses are disclosed. The compounds generally comprise a sulfamate moiety and an aromatic, estrogen receptor blocker moiety. Methods for synthesizing these compounds and using them in the therapeutic and/or prophylactic treatment of an estrogen-dependent disease are also disclosed.

19 Claims, 5 Drawing Sheets

COMPOUNDS FOR THE TREATMENT OF ESTROGEN-DEPENDENT ILLNESSES AND METHODS OF MAKING AND USING THE SAME

CROSS REFERENCE TO RELATED APPLICATION

This application is a divisional application of U.S. application Ser. No. 09/536,331, filed Mar. 24, 2000 now U.S. Pat. No. 6,288,107, which is a continuation-in-part of U.S. application Ser. No. 09/164,889, filed Oct. 1, 1998 now U.S. Pat. No. 6,248,780, for "Compounds for the Treatment of Estrogen-Dependent Illnesses and Methods for Making and Using the Same", the contents of which are hereby incorporated by reference.

FIELD OF THE INVENTION

The present invention relates to compounds for treatment of estrogen-dependent illnesses and methods for making and using the same. The compounds generally function by inhibiting sulfatase and/or blocking estrogen receptors. Methods of using these compounds provide both therapeutic and prophylactic treatment for estrogen dependent illnesses.

BACKGROUND OF THE INVENTION

Breast cancer is the most common malignancy in the United States. Clinically, breast cancer is divided into two types as defined by the amount of estrogen receptor (ER) present: estrogen dependent (ER+) and estrogen independent (ER−). It is estimated that approximately 30–40% of all breast cancers are estrogen dependent, and in postmenopausal women, the percentage is even higher. The most common treatment for estrogen-dependent breast cancers are endocrine treatments using an antiestrogen, such as tamoxifen, which blocks estrogen receptors. Progestins are also used although their mechanism of action is unknown. Other methods for treating estrogen-dependent breast cancer is through inhibition of estrogen biosynthesis with aromatase inhibitors. Aminoglutethimide, a non-steroidal aromatase inhibitor, and testolactone, a weak steroid aromatase inhibitor, are examples of compounds that have been used. Another non-steroidal aromatase inhibitor, CGS 16949A, and a steroidal aromatase inhibitor, 4-hydroxy-androstenedione, are at various stages of clinical trials.

All of the treatments described above deal with stopping the estrogen action through blocking estrogen receptors or inhibiting estrogen production. In estrogen dependent breast cancer patients, the estrogen levels in breast cancer cells are 5–10 times higher than in plasma. In postmenopausal women, the major pathway of estrogen production is through peripheral aromatization of circulating androstenedione (A) to estrone (E1), an estrogen with moderate biological activity. Estrone can be converted to estradiol (E2), the most potent endogenous estrogen, by 17β-hydroxysteroid dehydrogenase. The mean plasma levels of E1 and E2 in postmenopausal women are 100–150 μM and 30–40 pM, respectively.

Breast cancer cells accumulate high amounts of estrogens, even though studies have shown that there is no active uptake of estrogens by breast tumors. One of the possibilities to explain the high levels of estrogen is in situ production of estrogens from precursor substrates in the breast cancer cells. Indeed, aromatase has been found in breast cancer cells and conversion of androstenedione to estrone has been demonstrated. Another pathway for the in situ formation of estrogen is through the conversation of estrone sulfate (E1S) to estrone by the enzyme estrone sulfatase (estrone sulfatase pathway) as shown in FIG. 1. Estrone sulfate is the most abundant circulating estrogen in women (1–2 nM), which may represent an important reservoir of active estrogens.

The plasma level of estrone sulfate in postmenopausal breast cancer patients is reported to be significantly higher than in normal subjects. In addition, the concentration of estrone sulfate in the breast cancer cells of postmenopausal breast cancer patients is significantly higher than in plasma. Furthermore, estrone sulfatase has been consistently found in human breast cancer cells. High concentrations of estrone sulfate in blood and in breast cancer cells may provide a high flux of free estrogen to mammary tumors. Vignon et al., *Endocrinology* 106:1079–1086 (1980), demonstrated that in the MCF-7 human breast cancer cell line, estrone sulfate entered the cells and was metabolized, yielding unconjugated estrone and estradiol which were finally bound to nuclear estrogen receptors and eventually induced proteins of 46,000 and 160,000 molecular weight. Wilking et al., *␣Eur.J. Cancer* 16:1339–1344 (1980), were able to demonstrate the conversion of [$^3$H] estrone sulfate to [$^3$H] estrone and [$^3$H] estradiol by homogenates of mammary carcinoma tissue in vitro in 23 breast cancer patients. Pasqualini et al., *J. Steroid Biochem.* 34:155–163 (1989), reported that a high percentage of [$^3$H] estrone sulfate was converted to estradiol in different hormone-dependent mammary cancer cell lines (MCF-7, R-27, T-47D), but little or no conversion was found in the hormone-independent mammary cancer cell lines (MDA-MB-231, MDA-MB-436). Santen et al., *J. Clin. Endocrinol. & Metab.* 59:29–33 (1984), and *Am. NY Acad. Sci.* 464:126–137 (1986), evaluated the estrogen production from breast tumors via the estrone sulfate to estrone (sulfatase) pathway and compared it with the androstenedione to estrone (aromatase) pathway. When comparing the sulfatase with aromatase activity in human tumors at physiological levels of substrates, the amount of estrone produced through sulfatase was 10 times higher than through the aromatase pathway (2.8 pmol estrone/g protein vs 0.27 pmol/g protein) in human breast tumors. Santen suggested that this sulfatase pathway was significant and perhaps the primary means of local estrogen production in breast tumor tissues. In addition, despite the fact that aromatase inhibitors can cause a near total inhibition (95–98%) of peripheral aromatization of androstenedione to estrone, plasma levels of estrone and estradiol are sustained at a level of 45–65% and estrone sulfate at 40–50%, the control levels in patients receiving aromatase inhibitor treatments. This residual amount of estrone sulfate may be a potential source of estrogens through the sulfatase pathway.

Preliminary reports indicate the importance of the estrone sulfatase pathway in supplying estrogenic steroids to support breast cancer growth. Inhibitors of this pathway may be potential therapeutic agents for the treatment of estrogen-dependent breast cancer. Among all the estrone sulfatase inhibitors, estrone-3-O-sulfamate (EMATE) is the most potent sulfatase inhibitor ever reported. It is classified as an active-site directed irreversible inhibitor. Estrone may be released during the inactivation of sulfatase by EMATE, however, thereby making the inhibitor itself estrogenic. This compound is therefore not useful in the treatment of estrogen-dependent illnesses.

Reed and co-workers reported the sulfatase inhibitory activities of estrone-3-O-methylthiophosphonate, estrone-3-O alkyl and aryl sulfonates, estrone-3-O-phosphonates and thiophosphonates and estrone sulfamates in: Duncan et al., "Inhibition of estrone sulfate activity by estrone-3- methylthiophosphonate", *Cancer Res.* 53:298–303 (1993); Howarth et al., "Phosphonates and thiophosphonates as sulfate surrogates: Synthesis of estrone-3-methylthiophosphonate, a potent inhibitor of estrone sulfatase", *Bioorg. Med. Chem. Lett.* 3:313–318 (1993); Howarth et al., "Estrone sulfamates: Potent inhibitors of estrone sulfatase with therapeutic potential", *J. Med. Chem.* 37:219–221 (1994); and Purohit, et al., "In vivo inhibition of Oesterone Sulphatase and Dehydoepiandrosterone Sulphatase by Oestrone-3-O-sulphamate", *Int. J. Cancer*, 63:106–111 (1995).

Li and co-workers reported the synthesis and sulfatase inhibitory activities of sulfonate and its analogues, methylene sulfonates and phosphates that contain the estrone nucleus in Li et al., "Synthesis and biochemical studies of estrone sulfatase inhibitors", Steroids, 58:106–111 (1993); Dibbelt et al, "Inhibition of human placental sterylsulfatase by synthetic analogues of estrone sulfate", *J. Steroid Biochem. Molec. Biol.*, 52 (3):281–286 (1995); and Li et al., "Estrone sulfate analogues as estrone sulfatase inhibitors", *Steroids* 60:299–306 (1995). Estrone-3-amino derivatives are reported in Selcer et al., "Inhibition of Placental Estrone Sulfatase Activity and MCF-7 Breast Cancer Cell Proliferation by Estrone-3-amino Derivatives", *J. Steroid Biochem. Molec. Biol.*, 59:83–91 (1996).

U.S. Pat. No. 5,567,831 is directed to the use of non-steroidal sulfatase inhibitor compounds in the treatment of estrogen dependent illnesses.

U.S. Pat. No. 5,571,933 is directed to derivatives of estra 1,3,5(10)triene-17-one, 3-amino compounds and methods for using these compounds in the treatment of estrogen dependent illnesses.

U.S. Pat. Nos. 5,556,847 and 5,763,492 are directed to steroidal and non-steroidal sulfatase inhibitors, respectively, and methods for using these inhibitors to effect memory enhancement. Use of these inhibitors in the treatment of estrogen dependent illnesses is not disclosed.

U.S. Pat. No. 5,616,574 discloses steroid sulphatase inhibitors and methods of using the same. The compounds are potent estrogens and metabolize to form estrones, in contrast to the compounds of the present invention.

U.S. Pat. No. 5,047,431 discloses derivatives of 1,1,2-triphenylbut-1-ene, also known as tamoxifen. The '431 compounds have a hydroxy group attached at the 3° position of the phenyl ring on the C-atom 1 with respect to the position of the unsubstituted phenyl group on the C-atom 2 of the double bond.

U.S. Pat. No. 5,273,993 discloses compounds having at least one aminosulfonyloxy radical and the use of such compounds in the treatment of chronic arthritis or osteoporosis.

There remains a need for potent sulfatase inhibitors that are metabolically stable, more selective and devoid of estrogenic activity.

SUMMARY OF THE INVENTION

The present invention has met the above described needs by providing compounds useful as steroid sulfatase inhibitors. The present compounds offer a further benefit over the compounds reported in the art in that they also have ability to block estrogen receptors. These compounds have the general formula:

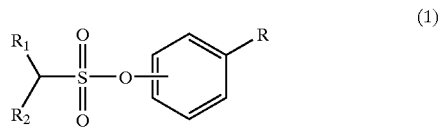

wherein the aromatic ring together with the R group represent a moiety that blocks an estrogen receptor; wherein $R_1$ and $R_2$ are independently selected from the group consisting of hydrogen and a lower alkyl group having between about one and six carbons; and wherein the sulfamate group is attached to the 2'C, the 3'C or the 4'C. of the aromatic ring.

In addition, the present invention relates to methods for using the present compounds in the treatment of estrogen-dependent illnesses. These methods generally comprise incorporating one or more of the compounds into a suitable pharmaceutical carrier and administering a therapeutically or prophylactically effective amount of the compound to a patient.

It is an aspect of this invention to provide compounds for substantially inhibiting the steroid sulfatase enzyme produced in the body.

Another aspect of the invention is to provide compounds that block estrogen receptors.

It is a further aspect of the invention to provide compounds that function both as sulfatase inhibitors and estrogen receptor blockers.

It is a further aspect of the present invention to provide compounds having activity against estrogen dependent illnesses.

Yet another aspect of the invention is to provide methods for therapeutically or prophylactically treating a patient having an estrogen dependent illness.

It is another aspect of this invention to provide compounds for the treatment of estrogendependent illnesses that are not metabolized to compounds that are estrogenic.

These and other aspects of the invention will be more fully understood to those skilled in the art upon review of the following description and appended claims.

DETAILED DESCRIPTION OF THE INVENTION

Figure 1:
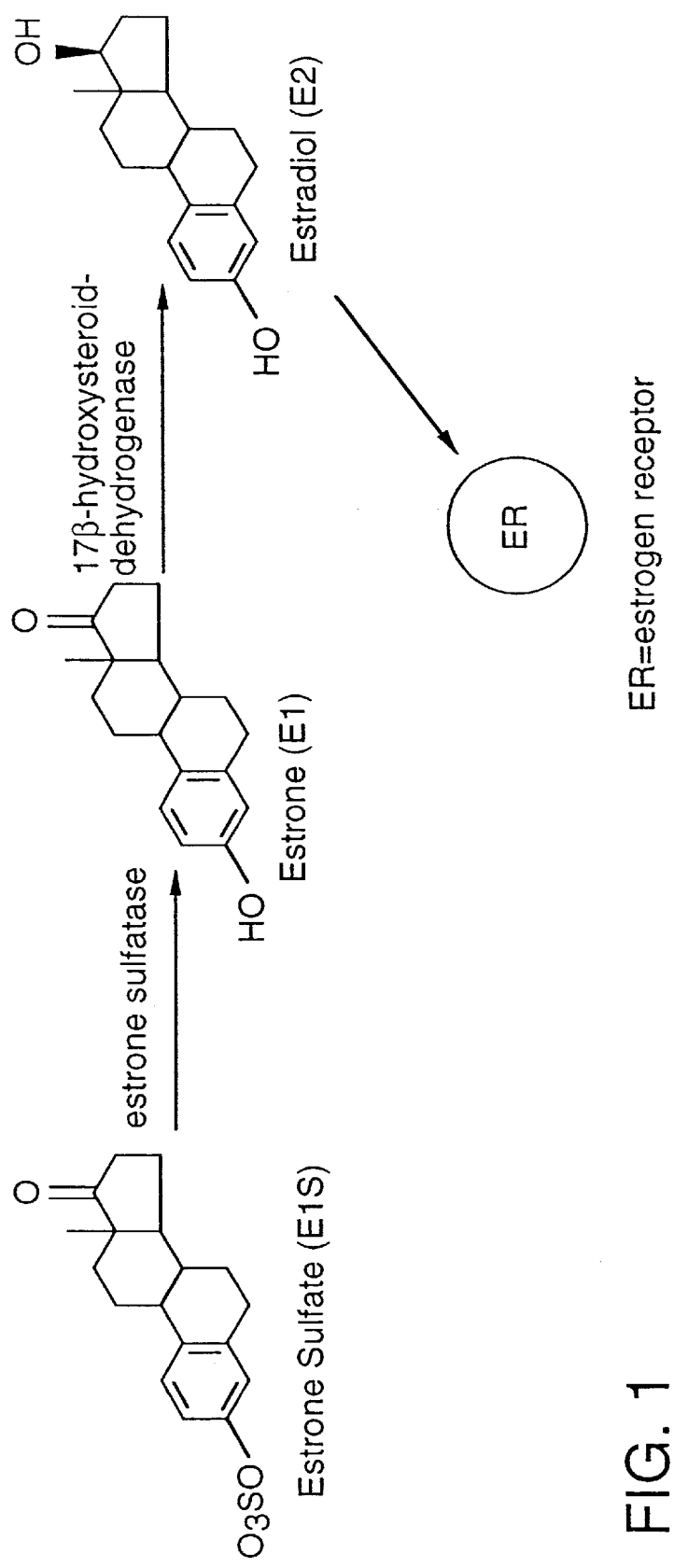
FIG. 1 generally illustrates the estrone sulfatase pathway.

As used herein, the term "patient" refers to members of the animal kingdom including but not limited to human beings.

The present invention relates to compounds having the formula (1):

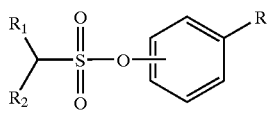

wherein the aromatic ring together with the R group represent a moiety that blocks an estrogen receptor; wherein $R_1$ and $R_2$ are independently selected from the group consisting of hydrogen and a lower alkyl group having one to six carbons; and wherein the sulfamate group is attached to the 2'C, the 3'C, or the 4'C of the aromatic ring.

A preferred embodiment of the above compound is represented by formula (2):

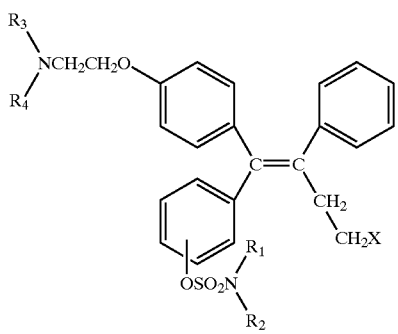

wherein $R_1$ and $R_2$ are independently selected from the group consisting of hydrogen and a lower alkyl group having 1 to 6 carbons; wherein $R_3$ and $R_4$ are independently selected from the group consisting of hydrogen and a lower alkyl group having 1 to 6 carbons or $R_3$ and $R_4$ together comprise a cyclic structure having 4 to 6 carbons; wherein X is selected from the group consisting of hydrogen, a lower alkyl group having 1 to 4 carbons, OH, $NH_2$ and a halogen selected from fluorine, chlorine, bromine and iodine; and wherein the sulfamate group is attached at either the 2', 3' or 4' position of the aromatic ring.

A variation of formula 2, also a preferred embodiment of the compounds of the present invention, is represented by formula (3):

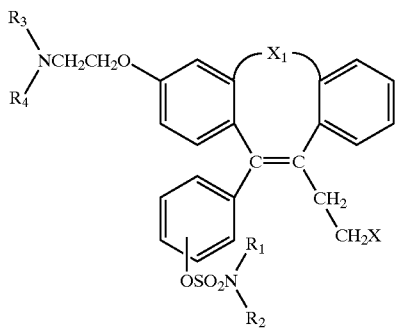

wherein $R_1$ through $R_4$ are as described above; X is as described above; $X_1$ is $(CH_2)_n$; and n equals 1 to 4.

In preferred embodiments of formulas 2 and 3, $R_3$ and $R_4$ equal $CH_3$, $R_1$ and $R_2$ equal H, X equals H or Cl and the sulfamate group is in the 4' position; for formula 3, n is preferably equal to 2.

As will be appreciated by those skilled in the art, the compounds of the present invention represented by formulas 2 and 3 are derivatives of (Z)-4-hydroxytamoxifen ("tamoxifen"). In these formulas, therefore, the moiety represented by the aromatic ring together with the R group, as shown in formula 1, is tamoxifen or a tamoxifen derivative. As used herein, the term "tamoxifen derivative" refers to compounds having the basic triphenylethylene structure of the tamoxifen molecule, but having the variations such as those defined above as $R_1$ through $R_4$, X, and $X_1$; other substituents and variations of the tamoxifen molecule are also within the scope of the present invention. Tamoxifen and its derivatives are known to block an estrogen receptor. The moiety represented by the aromatic ring to which is substituted an R group, as represented in formula 1, can be any compound that, like tamoxifen, functions to block estrogen receptors. Any estrogen receptor blocker having at least one aromatic ring to which can be attached a sulfamate group is therefore within the scope of the present invention. Examples include, but are not limited to, other triphenylethylene compounds. One skilled in the art could determine if a compound functions to block an estrogen receptor by utilizing the uterine weight gain assay described, for example, by Selcer and Li, *J. Steroid Biochem. Molec. Biol.*, Vol. 52, No. 3, pp. 281–286 (1995).

Another example of compounds within general formula 1 that are within the scope of the present invention are compounds having formula (4):

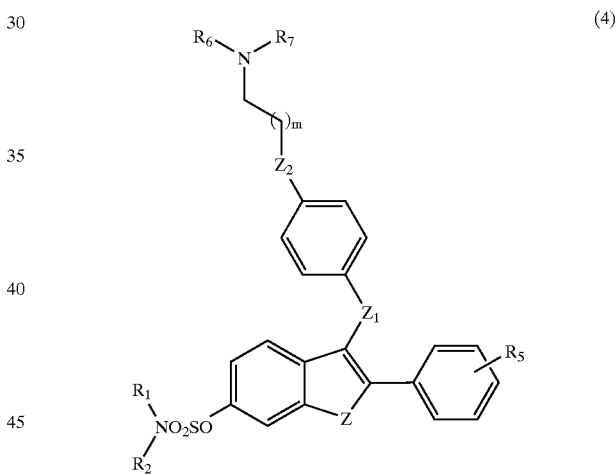

wherein $R_1$ and $R_2$ are as described above; Z is selected from the group consisting of O, S, NH, —C—C—, and —C=C—; $Z_1$ is selected from the group consisting of zero, O, NH, $CH_2$, and C=O; $Z_2$ is selected from the group consisting of O or $CH_2$; $R_5$ is selected from the group consisting of H, an alkyl group having one to three carbons, a halogen selected from fluorine, chlorine, bromine and iodine, a hydroxy group, an alkoxy group having one to three carbons, and $OSO_2 NR_1 R_2$ wherein $R_1$. and $R_2$ are as described above; m is 0 to 3; and $R_6$ and $R_7$ are independently selected from the group consisting of hydrogen and a lower alkyl group having 1 to 3 carbons or $R_6$ and $R_7$ together comprise a cyclic structure having the formula —$(CH_2)_q$- wherein q is 3 to 6. It will be understood that when $Z_1$ is zero that means there is no moiety at the $Z_1$. position and that the two rings having $Z_1$ there between are directly connected.

Preferred embodiments of formula 4 are those wherein $R_1$. and $R_2$ are both H, Z is S, $Z_1$ is C=O, $Z_2$ is O, m is 1, $R_6$ and $R_7$ are together $(CH_2)_q$ wherein q is 6 and wherein $R_5$ is selected from 4-$OSO_2NH_2$, H, 2-$CH_3$ or 4-F. Other preferred embodiments of formula 4 are those wherein $R_1$ and $R_2$ are both H, Z is —C—C—, $Z_1$ is zero, $Z_2$ is O, m is 1, $R_5$ is fixed at the 4 position and $R_5$, $R_6$ and $R_7$ are as defined in the following chart.

| $R_5$ | $R_6$ | $R_7$ |
|---|---|---|
| H | $CH_3$ | $CH_3$ |
| $CH_3$ | $CH_3$ | $CH_3$ |
| $OCH_3$ | $CH_3$ | $CH_3$ |
| OH | $CH_3$ | $CH_3$ |
| H | | —$(CH_2)_4$— |
| $CH_3$ | | —$(CH_2)_4$— |
| $OCH_3$ | | —$(CH_2)_4$— |
| OH | | —$(CH_2)_4$— |

Compounds having a pyrrolidinyl group typically have higher sulfatase inhibitory activity than compounds with dimethylamino groups.

The compounds of formula 4 provide advantages over other art known anti-estrogen compounds such as tamoxifen. More specifically, tamoxifen has been shown in vitro to isomerize into a mixture of Z and E isomers. The E isomer is estrogenic. The compounds of Formula 4 fix the "C=C" group found in the tamoxifen molecule, thereby preventing isomerization into an estrogenic molecule.

FIG. 1 depicts the production of estrogens through the estrone sulfatase pathway. As shown in that reaction scheme, estrone sulfate (ElS) is converted to estrone (E1) by the enzyme estrone sulfatase. Estrone is then converted to estradiol (E2) by the enzyme 17β-hydroxy steroid-dehydrogenase. The estradiol form of the compound is then able to bind with estrogen receptors stimulating tumor cell growth in estrogen-dependent forms of cancer.

Sulfamate compounds to which are attached a steroid ring system have been reported for the treatment of estrogen-dependent illnesses. The steroid ring system, or nucleus, is comprised of four rings, three of which are six membered (A, B and C) and one of which is five membered (D). As noted above, however, such compounds themselves break down to estrogen, thereby also contributing to the growth of the tumor cells. Such compounds function by inhibition of estrone sulfatase. It has been shown that the B, C and D rings of the steroid are not necessary for recognition of the sulfatase; all that is needed is the "A" ring of the steroid and the sulfamate moiety. The "A" ring will be understood by those skilled in the art as the aromatic ring in the steroid nucleus which is attached to the sulfamate moiety. The present compounds contain an aromatic ring attached to a sulfamate moiety. The sulfamate moiety recognizes and binds to the steroid sulfatase or estrone sulfatase, thereby preventing the conversion of estrone sulfate to estrone. Upon binding of the sulfate moiety with the enzyme, the aromatic ring portion of the present compounds, together with the R group, are believed to be released. The aromatic ring/R group moiety, which by definition is itself a compound that can block estrogen receptors, is then free to function in this manner. As noted above, blocking of estrogen receptors prevents estrogen from binding to the receptor, thereby preventing the estrogen from stimulating growth of cancer cells.

Although the inventors do not wish to be bound by any particular mechanism, it is believed that the compounds of the present invention have a two-fold effect in the treatment of estrogen-dependent illnesses: the sulfate moiety binds to and inhibits the steroid sulfatase activity; and an estrogen receptor blocker moiety binds to estrogen receptors thereby preventing estrogen molecules from attaching to estrogen receptors and promoting tumor cell growth. Thus, the effect of the compounds of the present invention is additive because the compound serves to inhibit estrogen production and stimulation of tumor cells in two ways.

Figure 2:
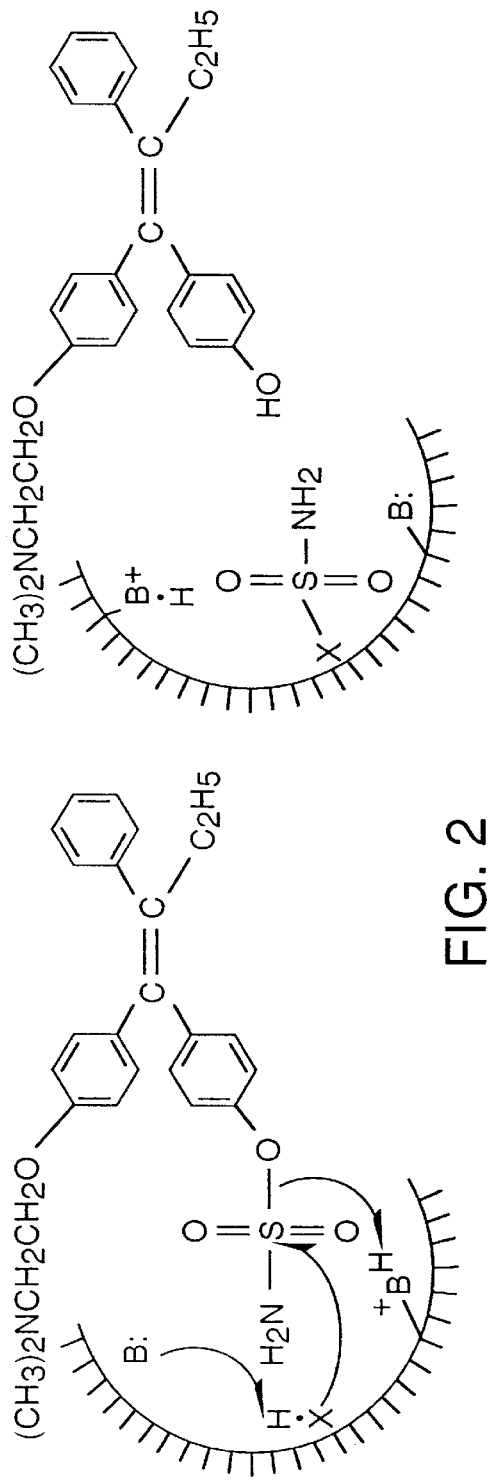
FIG. 2 illustrates the proposed mechanism of steroid sulfatase inactivation by (Z)-4-hydroxytamoxifen sulfamate.

A proposed mechanism of one embodiment of the present invention is depicted in FIG. 2. There, the aromatic ring/R moiety is tamoxifen. The sulfamate portion of the compound becomes bound to and inhibits the steroid sulfatase. Upon binding to the sulfatase, it is believed that the tamoxifen moiety is then released and is thereby free to block estrogen receptors.

Figure 3:
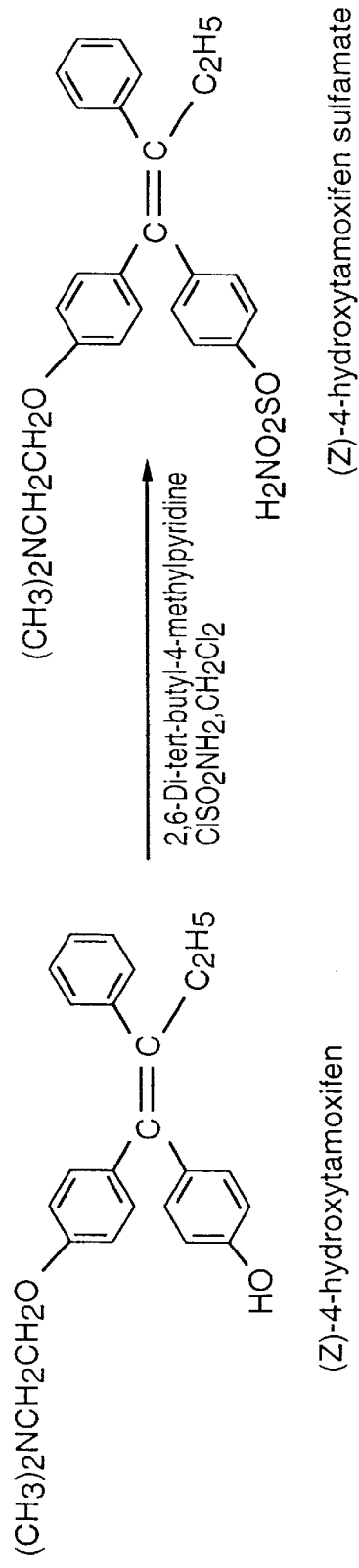
FIG. 3 illustrates the scheme for preparing compounds according to the methods of Example 1.

The present invention is further directed to the synthesis of the above-described compounds. This synthesis generally includes the addition of a sulfamate moiety to a nonsteroidal antiestrogen. The synthesis of one preferred compound is summarized in FIG. 3. FIG. 3 depicts use of (Z)-4-hydroxytamoxifen as the starting material to which is added 2,6-Di-tert-butyl-4-methylpyridine and sulfamoyl chloride. The result is a (Z)-4-hydroxy tamoxifen sulfamate compound. It will be appreciated that the synthesis of the compound as depicted in FIG. 3 is representative of the synthesis of all of the compounds of the present invention. The particular tamoxifen sulfamate compound prepared in FIG. 3 is generally represented by formula 2 above, wherein $R_1$ and $R_2$ are both hydrogen, $R_3$ and $R_4$ are both $CH_3$ and X is also hydrogen. The methods of synthesizing the sulfamate compounds of the present invention follow this general reaction scheme, which is described in more detail in the example section.

Figure 6:
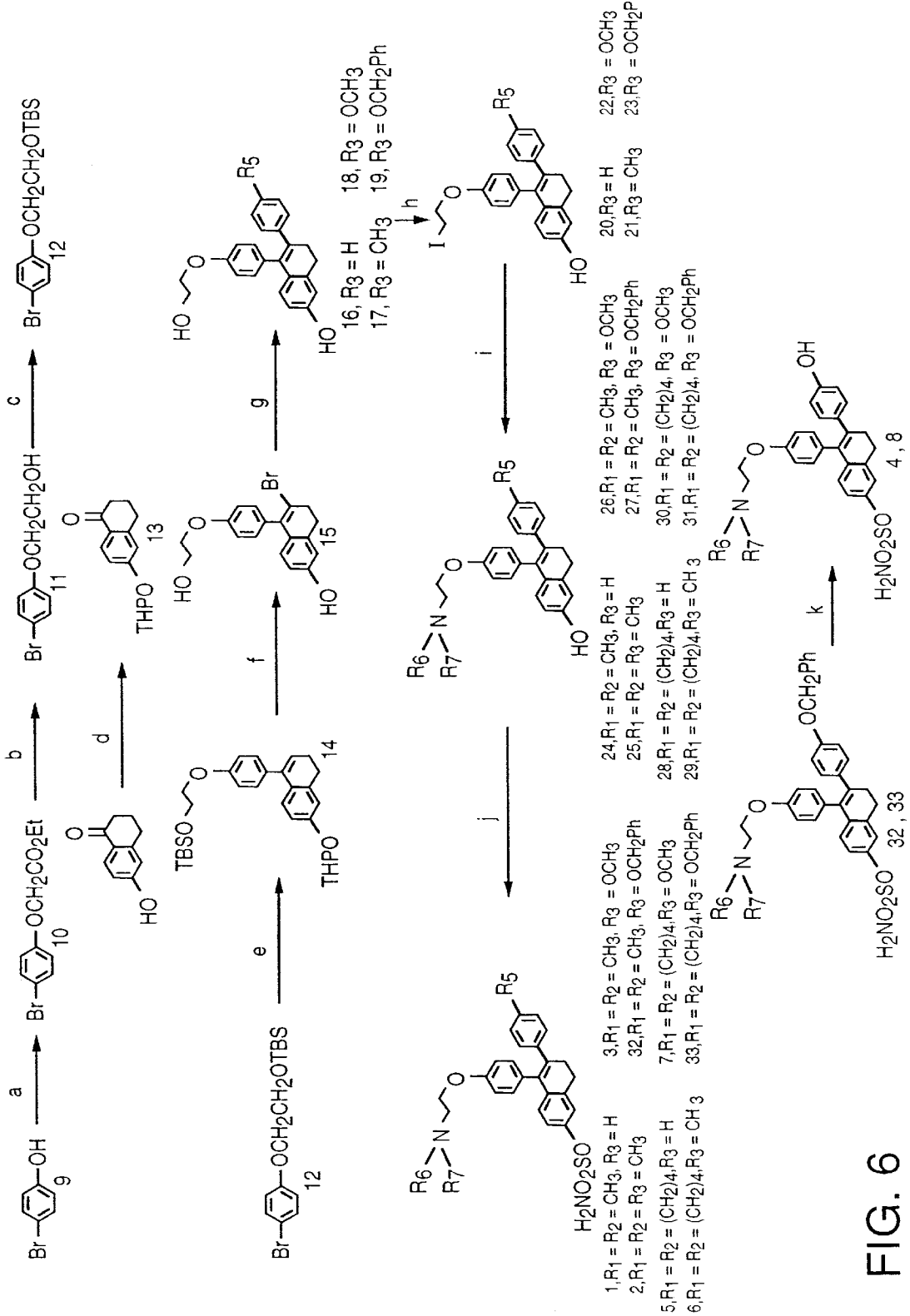
FIG. 6 shows a reaction scheme for preparation of compounds having formula 4, according to the methods of Example 4.

The synthesis of compounds having formula 4 is summarized in FIG. 6. More specifically, FIG. 6 shows a method of preparing preferred compounds having general formula 4 wherein $R_1$ and $R_2$ are both H, Z is —C—C—, $Z_1$ is zero, $Z_2$ is O, m is 1, $R_5$ is fixed at the 4 position, and $R_5$, $R_6$, and $R_7$ are as defined in the above chart. These compounds are specifically identified as compounds 1–8 in the figure. A more detailed description of the synthesis is found in the example section. It will be appreciated that the synthesis of the compounds as depicted in FIG. 6 are representative of the synthesis of all of the compounds having formula 4 and, more broadly, formula 1.

The present invention is further directed to methods for using the compounds described above to therapeutically and/or prophylactically treat a patient for an estrogen dependent illness. Such illnesses include, but are not limited to, breast cancer, vaginal cancer, endometrial cancer, ovarian cancer and endometriosis.

The methods of the present invention include the steps of: a) incorporating one or more of the compounds of the present invention in a suitable pharmaceutical carrier; and b) administering either a therapeutically effective dosage or a prophylactically effective dosage of the compound or compounds incorporated in the carrier to a patient.

The term "suitable pharmaceutical carrier" refers to any carrier known in the pharmaceutical arts for administration of compounds to a patient. Any suitable pharmaceutical carrier can be used according to the present invention, so long as compatibility problems do not arise. A preferred pharmaceutical carrier is physiologic saline (0.9% sodium chloride), 5% dextrose in water.

Administration of an effective dosage to a patient can be accomplished by parenteral injection, such as intravenously, intrathecally, intramuscularly or intra-arterially. The compounds can also be administered orally or transdermally, or by any other means known to those skilled in the art. Oral administration is preferred.

As used herein, the term "therapeutically effective amount" refers to that amount of one or more of the compounds of the present invention required to therapeutically treat a patient. Such treatment is appropriate in patients having an estrogen-dependent illness. Similarly, the term "prophylactically effective amount" refers to that amount of one or more of the compounds of the present invention needed to prophylactically treat a patient. Such treatment is appropriate in patients who, for example, undergo surgery to remove cancerous growths; the compounds of the present invention would be administered to inhibit growth of any tumorous cells that were not removed by the surgery or to inhibit growth of any new tumor cells which appear.

As will be appreciated by those skilled in the art, the dosage of compound given, the route of administration and the duration of therapy will be dependent upon the individual being treated, taking into consideration such factors as the particular estrogen dependent illness being treated, the body weight of the patient, other therapies being employed to treat the patient, and the condition, clinical response and tolerance of the patient. Dosage, administration, and duration of therapy can be determined by one skilled in the art upon evaluation of these and other relevant factors. A typical patient will be a post-menopausal female or pre-menopausal female who has been ovariectomized. Although the dosage and administration will vary from patient to patient, a typical dose will range between 1 mg and 2 mg per kg of body weight, and will be administered daily.

The present invention provides numerous advantages over treatments known in the art. Because the compounds of the present invention are believed to have both steroid sulfatase inhibition activity and estrogen receptor blocking activity, there are two means by which these compounds prevent the growth of estrogen-dependent tumors in cancers. As a result, the use of the compounds of the present invention provides an additive effect not seen with other drugs. In addition, many of the drugs which block estrogen receptors, such as tamoxifen, are known to be nontoxic to the patient thereby minimizing the negative effects associated with other chemotherapeutic regimes. Finally, the compounds of the present invention are nonsteroidal; therefore the breakdown of these compounds does not contribute to the production of more estrogen. These and other advantages of the invention will be apparent to those skilled in the art.

EXAMPLES

The following examples are intended to illustrate the invention and should not be construed as limiting the invention in any way.

For all of the examples, chemicals and silica gel were purchased from Aldrich Chemical Company (Milwaukee, Wis.). The chemicals were checked for purity by thin layer chromatography and NMR. Biochemicals, estrone and estrone sulfate were obtained from Sigma Chemical Company (St. Louis, Mo.). [6,7-$^3$H]Estrone sulfate was purchased from Dupont Company. Melting points were determined on a Thomas Hoover capillary melting point apparatus and were uncorrected. Proton NMR spectra were obtained with a Bruker WH-300 (300 MHz) spectrophotometer. Elemental analyses were performed by Atlantic Microlab Inc. (Norcross, Ga.). Radioactive samples were analyzed with a Packard Tri—Carb 4530 Liquid Scintillation Counter. The liquid scintillation cocktail was Ecolume (ICN, Costa Mesa, Calif.).

Example 1

Synthesis of (Z)-4-hydroxtamoxifen Sulfamate

To a solution of (Z)-4-hydroxytamoxifen (150 mg, 0.39 mmol) and 2,6-di-tert-butyl-4-methylpyridine (246 mg, 1.2 mmol) in $CH_2Cl_2$ (12 ml) was added sulfamoyl chloride (347 mg, 3 mmol) portionwise with stirring. After stirring for three hours, the solution was washed with water until neutral, dried over $Na_2SO_4$, and evaporated under reduced pressure to form yellowish residue. Purification of the residue by silica gel chromatography eluted with petroleum ether:ethyl acetate (4:1) gave the pure compound as a foam (168 mg, 93% yield). $^1$H NMR (300 MHz, DMSO-$d_6$) δ 0.85 (t, 3H, J=7.2 Hz, $CH_3$), 2.18 (s, 6H, $N(CH_3)_2$), 2.40 (q, 2H, J=7.2 Hz, $CH_2CH_3$), 2.54 (t, 2H, J=5.7 Hz, $CH_2N$), 3.90 (t, 2H, J=5.7 Hz, $CH_2O$), 6.61 (d, 2H, J=8.1 Hz, ArH), 6.75 (d, 2H, J=8.1 Hz ArH), 7.12–7.30 (m, 9H, ArH), 8.04 (brs, 2H, $NH_2$). Analysis calculated for $C_{26}H_{30}N_2O_4S \times 0.5\ CH_3COOC_2H_5$; C, 65.86; H, 6.75; N, 5.49; S, 6.28. Found C, 65.70; H, 6.51; N, 5.81; S, 6.28.

Example 2

Rat Liver Microcosm Sulfatase Assay Procedure

The (Z)-4-Hydroxytamoxifen sulfamate prepared according to Example 1 was tested in vitro using rat liver microcosm as a source of sulfatase.

Livers, obtained from juvenile female Sprague-Dawley rats, were minced with scissors in ice-cold 0.25M Tris-sucrose buffer (1:2 w:v) and homogenized with a Tissue Tearor using three 30 sec bursts. The nuclear fraction was pelleted by centrifugation at 1500×g for 15 min at 4° C. The supernatant was decanted and centrifuged at 10,000×g for 30 min at 4° C. to pellet the mitochondrial fraction. The resulting supernatant was removed and centrifuged at 100,000×g to yield the microsomal fraction. The microsomal pellet was resuspended in 50 mM Tris-HCl buffer (1:5 w:v) and protein from the microsomal suspension was determined by using the BCA assay.

$^3$H-estrone sulfate (53 Ci/mmol) was diluted in 50 mM Tris-HCl buffer and 50 µl (140,000 dpm) of the solution were added to all assay tubes. Radioinert estrone sulfate was dissolved in ethanol and then diluted into 50 mM Tris-HCl buffer. To achieve final concentrations of estrone sulfate, 100 µl of desired concentrations were added to the assay tubes. Compounds prepared according to Example 1 were dissolved in ethanol and then diluted in 50 mM Tris-HCl buffer. To achieve a final concentration of 10 µM, 50 µl of each compound were added to designated assay tubes. Tubes not having the compounds of Example 1 contained 50 µl of an equal concentration of ethanol and 50 mM Tris-HCl buffer. Rat liver microsomes were diluted with Tris-HCl buffer to 25 µg/300 µl buffer. The assay was initiated by addition of microsomes (300 µl) in 15 sec intervals to the tubes containing the compounds. Control samples with no inhibitors received the addition of microsomes while control samples with no membranes did not. After 20 min of incubation at 37° C., 500 µl of 0.1 N NaOH were added to all tubes in 15 sec intervals to quench the assay. Extraction of radiolabeled estrone was accomplished by adding 3 ml of toluene to each tube. The quenched samples were vortexed for 1 min and centrifuged at 1,500×g for 5 min. Two 500 µl aliquots of the organic phase were removed from each sample with the addition of four ml of scintillation cocktail. All aliquots were placed in the Packard Tri-Carb scintillation counter for determination of product formation. Each sample was run in duplicate. Product formation for samples containing an inhibitor was compared to that of the control samples, and data for Km and Ki were assessed through Michaelis Menten and Lineweaver-Burk calculations. Km is the dissociation constant of the enzyme-substrate complex. Ki is the dissociation constant of enzyme-inhibitor complex. Results are shown in FIG. 4.

Figure 4:
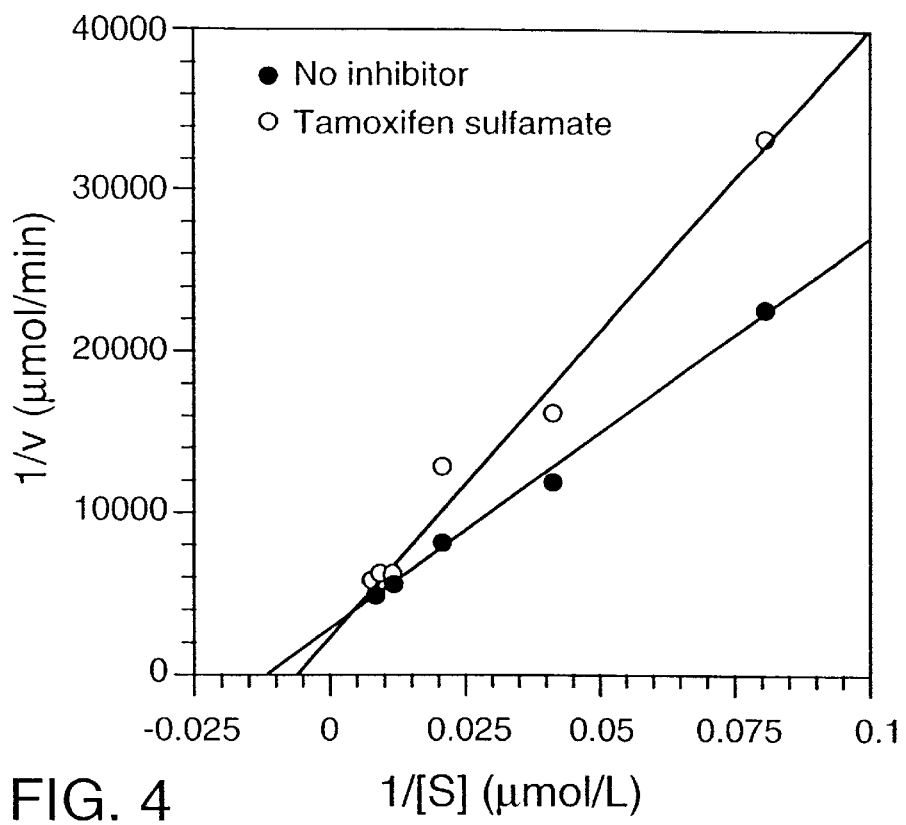
FIG. 4 is a double reciprocal plot demonstrating the inhibition of estrone sulfatase activity in rat liver microsomes by tamoxifen sulfamate, determined according to the methods of Example 2.

FIG. 4 is a double reciprocal plot (Lineweaver-Burk) demonstrating the inhibition of estrone sulfatase activity in rat liver microsomes by tamoxifen sulfamate. In FIG. 4, the rate of enzyme reaction is measured in the absence of inhibitor and in the presence of a fixed concentration of inhibitor, and the two sets of data are compared on the double reciprocal plot. It is shown that the maximum velocity of the enzyme reaction does not change and the Km is increased. This demonstrates that tamoxifen sulfamate is a competitive inhibitor. Based upon this plot it was determined that the Ki of tamoxifen sulfamate was approximately 17 $\mu$M.

Example 3

Intact Breast Cancer Cell Estrone Sulfatase Assay

The ability of the compound prepared according to Example 1 to block hydrolysis of estrone sulfate was examined using intact monolayers of MDA-MB-231 breast cancer cells.

Figure 5:
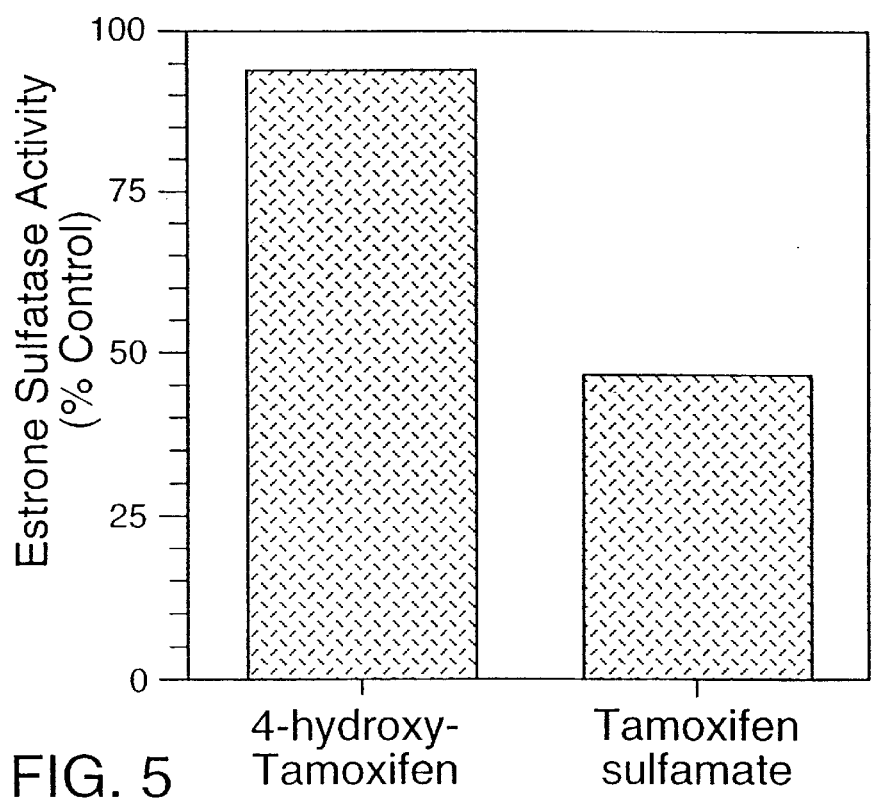
FIG. 5 is a graph comparing the inhibition of estrone sulfatase activity in human breast cancer cells by tamoxifen sulfamate and 4-hydroxytamoxifen, determined according to the methods of Example 3.

MDA-MB-231 cells were plated into 6-well dishes at approximately $1 \times 10^6$ cells/well in growth medium and incubated at 37° C. overnight to facilitate adherence to the plates. The growth medium contained 0.2% (v/v) sodium bicarbonate, 5% heat-inactivated fetal-calf serum, 10 mg/mL gentamicin, and 1% (v/v) antibiotic/antimycotic. Following incubation, growth medium was removed and replaced with growth medium containing $^3$H-estrone sulfate (100,000 dpm/ml), with or without the compound of Example 1 (10 $\mu$M). Cells were incubated for 18 h, then plates were cooled for 15 min. Medium from each well (500 $\mu$L) was aliquoted into 16×100 mm tubes. Three mls of toluene were added to each tube for extraction of unconjugated steroids. The tubes were vortexed for 1 min and then centrifuged at 2500×g for 5 min to separate the aqueous and organic phases. One mL of the organic phase (containing radiolabeled unconjugated steroids) was transferred to scintillation vials and 5 ml scintillation cocktail was added. Total radioactivity was counted using a Packard Tri-carb scintillation counter at 50% efficiency for $^3$H. All extractions were performed in duplicate and all treatments were run in triplicate. Product formation for samples containing an inhibitor was compared to that of the control samples run simultaneously and is reported as percent inhibition of control samples. Results are shown in FIG. 5, which indicates that at 10 $\mu$M concentration, tamoxifen sulfamate can inhibit about 50% of the estrone sulfatase in the breast cancer cells MDA-MB-231. Data in FIG. 5 are presented as percentage of control, which is estrone sulfatase activity in the absence of inhibitors.

Example 4

Synthesis of Conformational Restricted Analogs Having Formula 4

Reference letters and numbers correspond with those shown in FIG. 6 and/or are further identified below.
Synthesis of Compound 10

4-Bromophenol 9 (4.33 g, 25 mmol), ethylbromoacetate (4.25 ml, 37.5 mmol), $K_2CO_3$ (5.2 g, 37.5 mmol) in acetone (150 ml) was refluxed for 2.5 h, filtered, concentrated, yielding the target compound 10 (6.45 g, 99.3%). m.p: 56–58° C. $^1$H NMR (300 MHz, CDCl$_3$) $\delta$ 1.27 (t, 3H, J=7.2 Hz), 4.24 (q, 2H, J=7.2 Hz), 4.57 (s, 2H), 6.77 (d, 2H, J=9.0 Hz), 7.37 (d, 2H, J=9.0 Hz).

Synthesis of Compound 12

A solution of ethyl-2-(4-bromophenoxy)-acetoacetate (6.35 g, 24.6 mmol) in THF (40 ml) was added to the suspension of LiAlH$_4$ (1.4 g, 37 mmol) in THF (120 ml) at 0° C. The reaction mixture was stirred at r.t. for 2 h and then quenched carefully with H$_2$O and 15% NaOH, filtered, dried (Na$_2$SO$_4$), concentrated, affording the corresponding alcohol compound 11 which was using directly for the next step.

The crude compound 11 was dissolved in DMF (60 ml) and TBSCl (4.8 g, 31.9 mmol), imidazole (4.4 g, 64.7 mmol) was added. The reaction mixture was stirred overnight and diluted with ether (150 ml), washed with H$_2$O (3×80 ml), dried (Na$_2$SO$_4$) and concentrated. The residue was purified by chromatography, using petroleum ether: CH$_2$Cl$_2$ (3:2) as eluent, giving pure compound 12 (7.83 g, 96.4% for 2 steps) as an oil. $^1$H NMR (300 MHz, CDCl$_3$) $\delta$ 0.0087 (s, 6H), 0.81 (s, 9H), 3.87 (m, 4H), 6.69 (d, 2H, J=9.0 Hz), 7.26 (d, 2H, J=9.0 Hz).
Synthesis of compound 13

6-Hydroxytetralone (9.72 g, 60 mmol) in CH$_2$Cl$_2$ (300 ml) was reacted with dihydropyran (13.7 ml, 150 mmol) at r.t. for 2.5 h. The reaction mixture was washed with saturated NaHCO$_3$ (2×100 ml), H$_2$O (150 ml) and dried, concentrated to five crude THP ether compound 13 (14.17 g, 96%) which used directly for the next step.

Compound 12 (17.0 g, 51.5 mmol) in THF (300 ml) was treated with n-BuLi (1.6M, 32.5 ml, 52 mmol) at ÿ78° C. for 45 min. To the above solution was added a solution of compound 13 (8.19 g, 33.3 mmol) in THF (30 ml). The reaction mixture was slowly warmed to r.t. during 3 h and quenched with H$_2$O (150 ml), extracted with ethyl acetate (3×200 ml). The organic layers were combined, dried (Na$_2$SO$_4$) and concentrated. The residue was dissolved in CH$_2$Cl$_2$ (300 ml) and treated with silica gel and kept overnight. The residue was chromatographed using petroleum ether: EtOAc (6:1:1) as eluent, affording pure product compound 14 (10.5 g, 65.7%) as a gum. $^1$H NMR (300 MHz, DMSO-d$_6$) $\delta$ 0.081 (s, 6H), 0.88 (s, 9H), 1.54–1.82 (m, 6H), 2.30 (m, 2H), 2.73 (m, 2H), 3.53 (m, 1H), 3.75 (m, 1H), 4.04 (m, 2H), 5.46 (m, 1H), 5.89 (1H), 6.77–7.21 (m, 7H).
Synthesis of Compound 15

Compound 14 (960 mg, 2 mmol) in CH$_2$Cl$_2$ (10 ml) was treated with pyridinium tribromide (720 mg, 2.25 mmol) in the presence of Na$_2$HPO$_4$ (426 mg, 3 mmol) at 0° C. The reaction mixture was stirred at 0° C. for 1.5 h and washed with H$_2$O (2×10 ml), dried (Na$_2$SO$_4$) and concentrated. The residue was dissolved in THF (15 ml) and 2 N HCl (30 ml) was added. The mixture was stirred at r.t. for 1.5 h and concentrated. The residue was extracted with CH$_2$Cl$_2$ (3×40 ml). The organic layers were combined and concentrated. The residue was purified by chromatography using petroleum ether: ethyl acetate (2:1) as eluent, yielding pure bromide compound 15 (650 mg, 90.3%) m.p: 128° C. (dec.) $^1$H NMR (300 Mz, DMSO-d$_6$) $\delta$ 2.86 (m, 4H), 3.73 (m, 2H), 4.02 (t, 2H, J=4.8 Hz), 4.88 (br s, 1H), 6.33 (d, 1H, J=8.4 Hz), 6.44 (dd, 1H, J=1.8, 8.4 Hz) 6.60 (d, 1H, J=1.8 Hz), 6.98 (d, 2H, J=8.7 Hz), 7.06 (d, 2H, J=8.7 Hz), 9.49 (s, 1H).
Synthesis of Compound 16

To a solution of ZnCl$_2$ (1.88 g, 13.82 mmol) in THF (50 ml) at 0° C. was added PhLi (1.8 M, 7.73 ml, 13.9 nunol). The reaction mixture was stirred for 30 min. To this mixture was added a solution of compound 15 (920 mg, 2.56 mmol) in THF (10 ml), Pd(PPh$_3$)$_4$ (60 mg). The reaction mixture was refluxed for 2.5 h and then quenched with sat. NH$_4$Cl (80 ml) and extracted with EtOAc (2×100 ml). The organic layers were dried (Na$_2$SO$_4$) and concentrated. The residue was purified by chromatography with pet.ether:

EtOAc:CH$_2$Cl$_2$ (2:1:2) as eluent, giving pure compound 16 (860 mg, 94%). m.p: 138–140° C.; $^1$H NMR (300 MHz, DMSO-d$_6$) δ 2.65–2.83 (m, 4H), 3.69 (m, 2H), 3.92 (t, 2H, J=4.8 Hz), 4.85 (br s, 1H), 6.44–7.13 (m, 12H), 9.41 (s, 1H).

Synthesis of Compound 20

Compound 16 (830 mg, 2.32 mmol) in CH$_2$Cl$_2$ (80 ml) was treated with PPh$_3$ (2.2 g, 8.4 mmol), I$_2$ (2.1 g, 8.27 mmol) and imidazole (580 mg, 8.53 mmol) at r.t. for 45 min. Saturated NaHCO$_3$ (50 ml) was added to the reaction mixture and stirred for 20 min. The organic layer was separated and washed with sat. Na$_2$SO$_3$ (2×40 ml) and dried (Na$_2$SO$_4$), concentrated. The residue was purified by flash chromatography using pet ether: EtOAc:CH$_2$Cl$_2$ (6:1:6) as eluent, affording iodide compound 20 (1.03 g, 95%) which was used immediately for the next step.

Synthesis of Compound 24

Iodide 20 (468 mg, 1 mmol) was reacted with (CH$_3$)$_2$NH (2.0M, 24 ml, 12 mmol) in the presence of K$_2$CO$_3$ (138 mg, 1 mmol) at r.t. overnight. The reaction mixture was diluted with CH$_2$Cl$_2$ (40 ml) and washed with H$_2$O (2×20 ml). The organic layer was separated and dried (Na$_2$SO$_4$), concentrated. To the residue was added a mixture of pet ether: EtOAc (6:1). It was filtered and the solid was washed with pet ether: EtOAc (6:1) to give pure amine compound 24 (340 mg, 88.3%). m.p: 138–139° C. $^1$H NMR (300 MHz, DMSO-d$_6$) δ 2.20 (s, 6H), 2.59–2.82 (m, 6H), 3.98 (t, 2H, J=5.7 Hz), 6.45–7.12 (m, 12H), 9.42 (s, 1H).

Synthesis of Compound 28

Similar to the synthesis of compound 24, reacting iodide 20 with pyrrolidine (3 ml) in the presence of K$_2$CO$_3$ (152 mg) yielded compound 28 (395 mg, 90%). m.p: 171–173.5° C.; $^1$H NMR (300 MHz, DMSO-d$_6$). δ 1.65–1.80 (m, 4H), 2.50–3.04 (m, 1OH), 4.01 (t, 2H, J=6.0 Hz), 6.44–7.12 (m, 12H).

Synthesis of Inhibitor 1

Compound 24 (154 mg, 0.4 ml) in CH$_2$Cl$_2$ (15 ml) was treated with 2,6-di-tert-butyl-4-methylpyridine (470 mg) followed by sulfamoyl chloride which was prepared by treatment of ClSO$_2$NCO (0.36 ml) with HCOOH (0.16 ml). The reaction mixture was stirred at r.t. for 1 h and the sat. NaHCO$_3$ (15 ml) was added. The organic layer was separated, dried (Na$_2$SO$_4$) and concentrated. The residue was purified by chromatography using CH$_2$Cl$_2$:CH$_3$OH (10:1) as eluent, affording pure inhibitor 1 (170 mg, 91.6%). m.p: 95–97° C.; $^1$H NMR (300 MHz, DMSO-d$_6$) δ 2.20 (s, 6H), 2.60–2.92 (m, 6H), 3.99 (t, 2H, J=5.7 Hz), 6.66–7.18 (m, 12H), 7.98 (br s, 2H).

Synthesis of Inhibitor 5

Similar to the synthesis of Compound 1, Compound 28 (165 mg, 0.4 mmol) was sulfamoylated with sulfamoyl chloride to yield inhibitor 5 (180 mg, 91.8%). m.p: 146–147° C.; $^1$H NMR (300 MHz, DMSO-d$_6$) δ 1.63 (m, 4H), 2.44–2.90 (m, 10H), 3.97 (t, 2H, J=5.7 Hz), 6.60–7.12 (m, 12H), 7.93 (br s, 2H).

Example 5

Sulfatase Inhibitory Activity of Conformational Restricted Analogs Having Formula 4

Inhibitor compounds 1–8 were prepared according to Example 4 and as shown in FIG. 6. For all of Compounds 1–8, R$_1$ and R$_2$ are H, Z is —C—C—, Z$_1$ is zero, Z$_2$ is CH$_2$, N is 0, and R$_5$, R$_6$ and R$_7$ are:

| Compound | R$_5$ | R$_6$ | R$_7$ |
| --- | --- | --- | --- |
| 1 | H | CH$_3$ | CH$_3$ |
| 2 | CH$_3$ | CH$_3$ | CH$_3$ |
| 3 | OCH$_3$ | CH$_3$ | CH$_3$ |
| 4 | OH | CH$_3$ | CH$_3$ |
| 5 | H | —(CH$_2$)$_4$— | |
| 6 | CH$_3$ | —(CH$_2$)$_4$— | |
| 7 | OCH$_3$ | —(CH$_2$)$_4$— | |
| 8 | OH | —(CH$_2$)$_4$— | |

Inhibitors 1–8 can be divided into two series. Both series have the same modifications at the para position (R$_5$) of the 2-phenyl group. Series 1 (inhibitors 1–4) contain the dimethylamino ethyl moiety while series 2 (inhibitor 5–8) have the pyrrolidinyl ethyl moiety. Inhibitors 1–8 were tested for their ability to inhibit estrone sulfatase activity of rat liver microsomes at 20 μM substrate estrone sulfate.

The sulfatase activity was determined as follows. The final volume of the enzyme assay was 0.15 ml. [6.7-3H] estrone sulfate (final concentration 20 μmole/L; 300,000 dpm/tube). An inhibitor (20 μmol/L final concentration) in DMSO and rat liver microsome 200 μg/tube in phosphate buffered saline, containing 0.25 M sucrose and 0.04 M nicotinamide, pH 7, were added to a 1.5 ml microtube. The assay began by the addition of the substrate estrone sulfate. After 20 minutes of incubation at 37° C., 0.5 ml of toluene were added to quench the assay. Control sample with no inhibitor were incubated simultaneously. Blank samples were obtained by incubating without estrone sulfatase. The quenched samples were vortexed for 30 seconds and centrifuged (9,000 rpm for 5 minutes). Two hundred and fifty microliter of toluene was obtained from each quenched samples to determine the amount of product formation. Product formation for samples containing an inhibitor was compared to that of control samples (without inhibitors) run simultaneously. This was reported as percent inhibition of control sample which equals $$100\% \times \frac{\text{Product formation for sample containing inhibitor}}{\text{Product formation for sample with no inhibitor (control)}}$$

Figure 7:
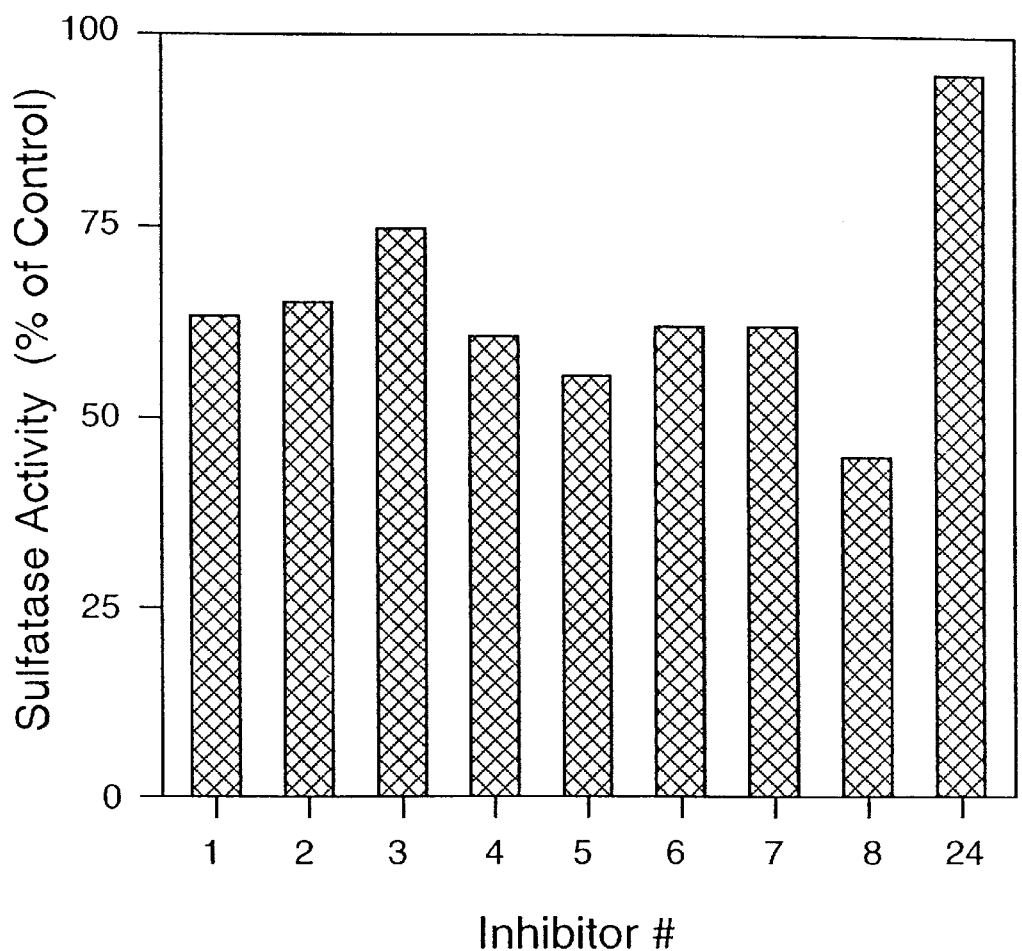
FIG. 7 shows sulfatase inhibitory activity of compounds having formula 4, determined according to Example 5.

FIG. 7 shows the relative inhibition of estrone sulfatase by the inhibitors. All the inhibitors significantly inhibited estrone sulfatase activity. The sulfamate moiety would appear to be necessary for sulfatase inhibition since compound 24, the precursor of inhibitor 1, did not show sulfatase inhibitory activity (FIG. 7). Varying the nature of the substituents in R$_5$ (H, CH$_3$, OCH$_3$, OH) has little effect on the sulfatase inhibitory activity. However, inhibitors with pyrrolidinyl group (inhibitors 5–8) consistently exhibit higher sulfatase inhibitory activities than the inhibitors with dimethylamino groups (inhibitor 1–4).

Whereas particular embodiments of this invention have been described above for purposes of illustration, it will be evident to those skilled in the art that numerous variations of the details of the present invention may be made without departing from the invention as defined in the appended claims.

What is claimed is:

1. A compound having the formula (4):

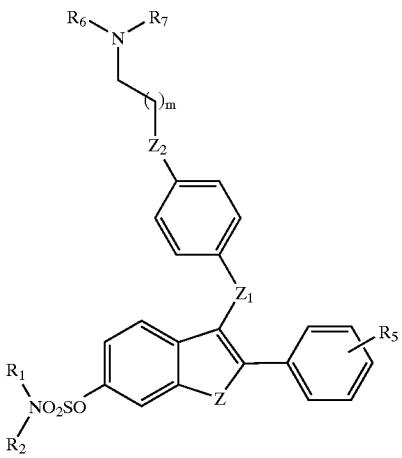

(4)

wherein $R_1$ and $R_2$ are independently selected from the group hydrogen and a lower alkyl group having one to six carbons; Z is selected from the group consisting of NH, —C—C—, and —C=C—; $Z_1$ is selected from the group consisting of zero, O, NH, $CH_2$, and C=O; $Z_2$ is selected from the group consisting of O or $CH_2$; $R_5$ is selected from the group consisting of H, an alkyl group having one to three carbons, a halogen selected from fluorine, chlorine, bromine and iodine, an alkoxy group having one to three carbons, and $OSO_2 NR_1 R_2$ wherein $R_1$ and $R_2$ are as described above; m is 0 to 3; and $R_6$ and $R_7$ are independently selected from the group consisting of hydrogen and a lower alkyl group having 1 to 3 carbons or $R_6$ and $R_7$ together form a cyclic structure having the formula —$(CH_2)q$— wherein q is 3 to 6.

2. The compound of claim 1 wherein $R_1$ and $R_2$ are both H, Z is —C—C—, $Z_1$ is zero, $Z_2$ is $CH_2$ and n is O.

3. The compound of claim 2 wherein $R_5$ is H, $R_6$ is $CH_3$, and $R_7$ is $CH_3$.

4. The compound of claim 2 wherein $R_5$ is $CH_3$, $R_6$ is $CH_3$ and $R_7$ is $CH_3$.

5. The compound of claim 2 wherein $R_5$ is $OCH_3$, $R_6$ is $CH_3$, and $R_7$ is $CH_3$.

6. The compound of claim 2 wherein $R_5$ is OH, $R_6$ is $CH_3$ and $R_7$ is $CH_3$.

7. The compound of claim 2 wherein $R_5$ is H and $R_6$ and $R_7$ are together —$(CH_2)_4$—.

8. The compound of claim 2 wherein $R_5$ is $CH_3$ and $R_6$ and $R_7$ are together —$(CH_2)_4$—.

9. The compound of claim 2 wherein $R_5$ is $OCH_3$ and $R_6$ and $R_7$ are together —$(CH_2)_4$—.

10. The compound of claim 2 wherein $R_5$ is OH and $R_6$ and $R_7$ are together —$(CH_2)_4$—.

11. A method for treating a patient having an estrogen dependent illness comprising administering to said patient an effective amount of a compound having the following formula (4):

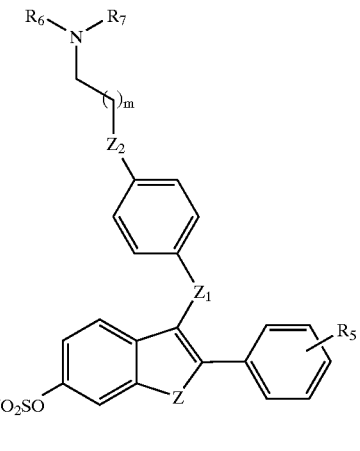

(4)

wherein $R_1$ and $R_2$ are independently selected from the group hydrogen and a lower alkyl group having one to six carbons; Z is selected from the group consisting of NH, —C—C—, and —C=C—; $Z_1$ is selected from the group consisting of zero, O, NH, $CH_2$, and C=O; $Z_2$ is selected from the group consisting of O or $CH_2$; $R_5$ is selected from the group consisting of H, an alkyl group having one to three carbons, a halogen selected from fluorine, chlorine, bromine and iodine, an alkoxy group having one to three carbons, and $OSO_2 NR_1 R_2$ wherein $R_1$ and $R_2$ are as described above; m is 0 to 3; and $R_6$ and $R_7$ are independently selected from the group consisting of hydrogen and a lower alkyl group having 1 to 3 carbons or $R_6$ and $R_7$ together form a cyclic structure having the formula —$(CH_2)q$- wherein q is 3 to 6.

12. The method of claim 11, wherein said compound is incorporated into a suitable pharmaceutical carrier.

13. The method of claim 12, wherein said suitably pharmaceutical carrier is physiologic saline, 5 percent dextrose.

14. The method of claim 11, wherein said treatment is selected from therapeutic treatment and prophylactic treatment.

15. The method of claim 11, wherein said administration is parenteral.

16. The method of claim 11, wherein said administration is oral.

17. The method of claim 11, wherein $R_1$ and $R_2$ are both H, Z is —C—C—, $Z_1$ is zero, $Z_2$ is $CH_2$ and n is O.

18. The method of claim 17, wherein $R_6$ and $R_7$ are both $CH_3$ and $R_5$ is selected from the group H, $CH_3$, $OCH_3$ and OH.

19. The method of claim 17, wherein $R_6$ and $R_7$ are together —$(CH_2)_4$— and $R_5$ is selected from the group H, $CH_3$, $OCH_3$ and OH.

* * * * *

UNITED STATES PATENT AND TRADEMARK OFFICE
CERTIFICATE OF CORRECTION

PATENT NO.     : 6,433,000 B1
DATED          : August 13, 2002
INVENTOR(S)    : Pui-Kai Li et al.

It is certified that error appears in the above-identified patent and that said Letters Patent is hereby corrected as shown below:

Column 1,
Line 58, "100-150 :M" should read -- 100-150 pM --.

Column 3,
Line 47, "3°" should read -- 3' --.

Column 9,
Line 64, "hydroxtamoxifen" should read -- hydroxytamoxifen --.

Column 12,
Line 60, "nunol" should read -- mmol --.

Column 14,
Line 23, "[6.7-3H]" should read -- [6.7-$^{3}$H] --.

Signed and Sealed this

Fourth Day of February, 2003

JAMES E. ROGAN
*Director of the United States Patent and Trademark Office*